United States Patent [19]

Ruwart

[11] 4,359,465
[45] Nov. 16, 1982

[54] METHODS FOR TREATING GASTROINTESTINAL INFLAMMATION

[75] Inventor: Mary J. Ruwart, Kalamazoo, Mich.

[73] Assignee: The Upjohn Company, Kalamazoo, Mich.

[21] Appl. No.: 173,233

[22] Filed: Jul. 28, 1980

[51] Int. Cl.³ ............................................. A61K 31/44
[52] U.S. Cl. ................................... 424/263; 424/250; 424/258; 424/267; 424/270; 424/273 R; 424/273 B
[58] Field of Search ............... 424/263, 258, 270, 273, 424/250, 273 B, 267

[56] References Cited

U.S. PATENT DOCUMENTS

| 3,781,429 | 12/1973 | Partridge et al. | 424/234 |
|---|---|---|---|
| 3,903,297 | 9/1975 | Robert | 424/305 |
| 3,927,213 | 12/1975 | Lippmann | 424/234 |
| 4,045,563 | 8/1977 | Berntsson et al. | 424/317 |
| 4,073,998 | 4/1978 | Robert | 424/317 |
| 4,081,553 | 3/1978 | Robert | 424/305 |
| 4,097,603 | 6/1978 | Robert | 424/317 |

FOREIGN PATENT DOCUMENTS 5129  3/1979  European Pat. Off.

OTHER PUBLICATIONS

C. Johansson, et al., "Mucosal Protection by Prostaglandin E$_2$", The Lancet, Feb. 2, 1979, p. 317.
M. M. Cohen, "Mucosal Cytoprotection by Prostaglandin E$_2$", The Lancet, Dec. 9, 1978, pp. 1253–1254.
Robert, A., "Cytoprotection Against Acidified Aspirin: Comparison of Prostaglandin, Cimetidine, and Probanthine", Gastroenterology 76: 1227 (May 1979).
Kauffman, G. L., et al., "Cimetidine Does Not Inhibit Indomethacin-Induced Small Bowel Ulceration in the Rat", Proc. of the Exp. Biol. Med. 161: 512–4 (1979).
Robert, A., "Method of Treatment and Prophylaxis of Gastric Hypersection and Gastric Duodenal Ulcers Using Prostaglandin Analogs", Prostaglandin Symposium of the Worcester Foundation for Experimental Biology, Oct. 16–17, 1967, Inter-Science, New York, 1978, p. 47.
Lars Olbe, et al., "Properties of a New Class of Gastric Acid Inhibitors", Scand. J. Gastroenterol., 14: 131–135 (1979, Supp 55).
Merck Index, 9th Edition, (APP-1 A-3).
Physicians' Desk Reference, 34th Edition (1980), pp. 1636–1641.

Primary Examiner—Sam Rosen
Attorney, Agent, or Firm—L. R. Hattan

[57] ABSTRACT

The present invention relates to the novel cytoprotective use for known heterocyclyalkylsulfinylbenzimidazoles, and novel, substantially non-antisecretory unit dose pharmaceutical compositions thereof.

5 Claims, No Drawings

METHODS FOR TREATING GASTROINTESTINAL INFLAMMATION

BACKGROUND OF THE INVENTION

The present invention relates to novel methods of treatment and compositions employed in such methods of treatment. The present invention particularly relates to novel methods for preventing or treating gastrointestinal inflammatory diseases.

Most particularly, the present invention relates to the surprising and unexpected cytoprotective effects of pharmacological agents heretofore known to be useful only for other actions on the gastrointestinal tract.

Certain pharmacological agents have heretofore been known to be useful in exerting a cytoprotective effect on the gastrointestinal tract. This cytoprotective effect is manifest in the ability of such compounds to treat or prevent non-traumatically-induced, non-neoplastic inflammatory diseases of the gastrointestinal tract. References describing such cytoprotective effects of prostaglandins are U.S. Pat. No. 4,083,998 (Robert, "Treatment of Inflammatory Diseases of the Mammalian large Intestine with Cytoprotective Prostaglandins"), issued Apr. 11, 1978, U.S. Pat. No. 4,081,553 (Robert, "Cytoprotective Prostaglandins for Use in Intestinal Diseases"), issued Mar. 28, 1978, and U.S. Pat. No. 4,097,603 (Robert, "Gastric Cytoprotection with Non-Antisecretory Doses of Prostaglandins"), issued June 27, 1978.

As indicated in the patents described above, gastrointestinal inflammatory diseases include gastric inflammatory diseases (such as gastric ulcer, duodenal ulcer and gastritis), and intestinal inflammatory diseases (including Crohn's disease, inflammatory bowel disease, tropical and non-tropical sprue, infectious enteritis, colitis, ulcerative colitis, pseudomembranous colitis, diverticulitis, and allergenic and radiological inflammatory diseases).

As is known in the art, gastrointestinal inflammatory diseases are characterized by inflammation, specifically by the presence of edema, characteristic inflammatory cells (i.e., leucocytes, histiocytes, and macrophages), and, in some cases, necrosis and ulceration of the surface epithelium. These inflammatory diseases are known to be caused by a wide variety of agents present in the gastrointestinal tract which are known to attack the surfaces thereof, producing the inflammatory disease response. Such agents include microorganisms (viruses and fungii), bacterial toxins, certain pharmaceutical agents (antibiotics and anti-inflammatory steroids), and chemical agents (bile salts, toxic household chemicals). Indeed, gastric acid itself is capable of attacking the stomach lining and producing the inflammatory state.

The prostaglandins and related fatty acid metabolites are a class of compounds from which most if not all the known cytoprotective agents are derived. Indeed, the endogenous production of prostaglandins by cells of the gastrointestinal tract apparently represents at least a part of a natural cytoprotective mechanism. For example, when a non-steroidal anti-inflammatory compound (NOSAC) is administered to a mammal, one effect is the inhibition of prostaglandin biosynthesis in the gastrointestinal tract, resulting in gastritis and gastrointestinal blood loss. However, when a prostaglandin is administered together with the non-steroidal anti-inflammatory compound, the untoward gastrointestinal consequences of NOSAC administration are alleviated. See U.S. Pat. No. 3,927,213 (Lippman, "Prostaglandin $E_2$ and Derivatives for Reducing the Side Effects of Anti-inflammatory Agents"), issued Dec. 16, 1975, and U.S. Pat. No. 3,781,429 (Partridge, "Method of Inhibiting Ulcerogenisis induced by Non-Steroidal Anti-Inflammatory Agents"), issued Dec. 25, 1973. Clinical reports of the reduction of gastrointestinal side effects from the concomitant administration of prostaglandins with NOSAC's are described by C. Johansson, et al., "Mucosal Protection by Prostaglandin $E_2$"), The Lancet, Feb. 10, 1979, p. 317, and M. M. Cohen, "Mucosal Protection by Prostaglandin $E_2$", The Lancet, Dec. 9, 1978, p. 1253–1254.

Another method of preventing or treating certain gastrointestinal diseases, specifically gastric diseases, is by inhibition of gastric acid secretion. In situations where the integrity of the gastric mucosal barrier is compromised, gastric acid secretion can result in erosion of the epithelial cells with consequent inflammation and ulceration. Inhibition of such untoward gastric acid-induced effects can be achieved by either neutralization of the effects of the acid (e.g., antacid administration), or by administration of a pharmacological agent effective to inhibit gastric acid secretion.

One class of such agents effective to inhibit gastric acid secretion are the gastric antisecretory prostaglandins. These substances are known to be effective in the treatment and cure of gastric and duodenal ulcers as a result of the inhibition of gastric secretion. See U.S. Pat. No. 3,903,297 (Robert, "Method of Treatment and Prophylaxis of Gastric Hypersection and Gastric Duodenal Ulcers Using Prostaglandin Analogs"), issued Sept. 2, 1975 and Robert, "Antisecretory Property of Prostaglandins", Prostaglandin Symposium of the Worcester Foundation for Experimental Biology, 16–17 October 1967, Inter-Science, New York, 1978, p. 47. Another important class of antisecretory agents are the histamine $H_2$ receptor antagonists, including metiamide and most especially cimetidine, N-cyano-N'-methyl-N''[2-[[(5-methyl-1H-imidazol-4-yl)methyl]thio]ethyl]gunanidine. See the Merck Index, 9th Edition, (APP-1 A-3) and Physicians' Desk Reference, 34th Edition, (1980), pages 1636–1641.

Accordingly, three classes of cytoprotective actions are known to affect beneficially gastrointestinal inflammatory diseases: (1) direct cytoprotective effects, such as those exhibited by the prostaglandins, (2) inhibitory effects on the untoward consequences of prostaglandin synthetase inhibition, e.g., such as are produced by NOSAC administration, and (3) inhibitory effects on the untoward effects of gastric acid secretion, such as are produced by antacids and gastric antisecretory agents such as prostaglandins and histamine $H_2$ receptor antagonists. Although the first of these three effects (protection from non-gastric acid and non-NOSAC induced inflammatory diseases) is the only one which can unconditionally be referred to as a "cytoprotective" effect, nonetheless both direct cytoprotective effects and the protective effects of the inhibition of untoward NOSAC-induced effects are commonly known in the art as "cytoprotective". Accordingly, the term "cytoprotective effect", "cytoprotective action", and "cytoprotection" as used herein will refer both to direct cytoprotection (U.S. Pat. Nos. 4,083,998, 4,081,553, and 4,097,603) and inhibition of NOSAC-induced effects (U.S. Pat. Nos. 3,927,213 and 3,781,429), but not protection against gastric-acid induced inflammatory diseases.

Although the prostaglandins represent a class of agents which, in some cases, are both "cytoprotective" and inhibitors of gastric secretion, not all gastric antisecretory agents exhibit appreciable cytoprotective effects. Moreover, antacids which effectively neutralize gastric acid are not cytoprotective. Cimetidine, for example, is an example of a highly potent inhibitor of gastric secretion, which is devoid of appreciable cytoprotective effects. See A. Robert, "Cytoprotection Against Acidified Aspirin: Comparison of Prostaglandin, Cimetidine, and Probanthine", Gastroenterology 76:1227 (May 1979), and references cited therein indicating any apparent cytoprotective effects of cimetidine are related to its antisecretory property. See also Kauffman, G. L., et al., "Cimeditine Does Not Inhibit Indomethacin-Induced Small Bowel Ulceration in the Rat", Proc. of the Soc. Exp. Biol. Med. 161:512–4 (1979).

The present invention specifically relates to heterocyclylalkylsulfinylbenzimidazoles, heretofore known to be useful as gastric antisecretory agents and, therefore, useful in the treatment of gastric ulcers. See U.S. Pat. No. 4,045,563 and European Published Patent Application No. 0 005 129 (abstracted and published as Derwent Farmdoc CPI No. 79478B). For at least certain of these substituted benzimidazoles, the inhibition of gastric secretion is accomplished by direct action on the acid-secreting parietal cells of the stomach, specifically through inhibition of potassium ion-dependent APTase. See, for example, Lars Olbe, et al., "Properties of a New Class of Gastric Acid Inhibitors", Scand. J. Gastroenterol, 14:131–135 (1979, Supp 55).

PRIOR ART

Heterocyclylalkylsulfinylbenzimidazoles are known in the art, as are methods of using these compounds to reduce gastric acid secretion. See the above references. Also known in the art are other gastric antisecretory agents, e.g., the prostaglandins and histamine $H_2$ receptor antagonists, such as cimetidine and metiamine. See also references cited above.

Finally, also known in the art are cytoprotective uses for certain prostaglandins, including gastric antisecretory prostaglandins. However, the absence of comparable cytoprotective effects for other gastric antisecretory agents unrelated to gastric antisecretory property is also known. See A. Robert, Gastroenterology 76:1227 (May 1979), cited above.

SUMMARY OF THE INVENTION

The present invention particularly provides (a) a method for the treatment or prevention of a non-gastric-acid-induced, non-traumatically-induced, non-neoplastic gastrointestinal inflammatory disease in a mammal suffering from or particularly susceptible to the development of said disease, which comprises:
administering orally to said mammal an amount of a cytoprotective heterocyclylalkylsulfinylbenzimidazole effective to treat or prevent said disease;

(b) an oral pharmaceutical composition in unit dosage form for the treatment or prevention of a non-gastric-acid-induced, non-traumatically-induced, non-neoplastic gastrointestinal inflammatory disease in a mammal suffering from or susceptible to the development of said disease which comprises:

(1) an amount of a cytoprotective heterocyclylalkylsulfinylbenzimidazole
  (a) effective to treat or prevent said disease, and
  (b) less than the gastric antisecretory $ED_{50}$ of said cytoprotective heterocyclylalkylsulfinylbenzimidazole; and
(2) a pharmaceutically-acceptable carrier; and (c) a method of protecting the gastrointestinal tract in a mammal from the untoward non-gastric-acid-induced effects of exposure to gastrointestinally injurious agents, which comprises:
administering orally to said mammal a non-antisecretory (less than antisecretory $ED_{50}$) amount of a cytoprotective heterocyclylalkylsulfinylbenzimidazole effective to prevent or ameliorate said effects.

Cytoprotective heterocyclylalkylsulfinylbenzimidazoles, together with the manner of making them and their pharmaceutical compositions for gastric antisecretory use are described in U.S. Pat. No. 4,045,563, incorporated by reference, and Appendix A, attached hereto, or European Published Application No. 0 005 152, published Oct. 31, 1979 (also abstracted and published at Derwent Farmdoc CPI No. 79478B).

Accordingly, said cytoprotective heterocyclylalkylsulfinylbenzimidazoles include a compound of formula I wherein $R_1$ and $R_2$, being the same or different, are
  (a) hydrogen,
  (b) alkyl of one to 4 carbon atoms, inclusive,
  (c) fluoro, iodo, chloro, or bromo,
  (d) cyano,
  (e) carboxy,
  (f) carboxyalkyl of 2 to 5 carbon atoms, inclusive,
  (g) alkoxycarbonyl of 2 to 5 carbon atoms, inclusive,
  (h) alkoxycarbonylalkyl of 3 to 9 carbon atoms, inclusive, with
the proviso that each alkyl group therein is of one to 4 carbon atoms, inclusive,
  (i) carbamoyl,
  (j) carbamoyloxy,
  (k) hydroxy,
  (l) alkoxy of one to 5 carbon atoms, inclusive,
  (m) hydroxyalkyl of one to 7 carbon atoms, inclusive,
  (n) trifluoromethyl, or
  (o) alkylcarbonyl of one to 4 carbon atoms, inclusive,
wherein $R_3$ is
  (a) hydrogen,
  (b) alkyl of one to 4 carbon atoms, inclusive,
  (c) alkylcarbonyl of one to 4 carbon atoms, inclusive,
  (d) alkoxycarbonyl of 2 to 5 carbon atoms, inclusive,
  (e) carbamoyl,
  (f) alkylcarbamoyl of 2 to 5 carbon atoms,
  (g) dialkylcarbamoyl of 3 to 9 carbon atoms, inclusive, with the
proviso that each alkyl is of one to 4 carbon atoms, inclusive,
  (h) alkylcarbonylmethyl of 3 to 5 carbon atoms, inclusive,
  (i) alkoxycarbonylmethyl of 3 to 5 carbon atoms, inclusive, or
  (j) alkylsulfonyl of one to 4 carbon atoms, inclusive;
wherein $X_1$ is alkylene of one to 4 carbon atoms, inclusive, with one to 4 carbon atoms, inclusive, in a chain, being straight or branched; and wherein Het is
  (a) imidazolyl,
  (b) imidazolinyl,
  (c) benzimidazolyl,
  (d) thiazolyl, (e) thiazolinyl,
(f) quinolyl,
(g) piperidyl,
(h) pyridyl, or
(i) imidazolyl, imidazolinyl, benzimidazolyl, thiazolyl, thiazolinyl, quinolyl, piperidyl, pyridyl, or pyridyl substituted by one, two, or 3 alkyl of one to 4 carbon atoms, inclusive, fluoro, iodo, chloro, or bromo, or wherein $R_1$ and $R_2$ are hydrogen, alkyl, halogen, methoxycarbonyl, ethoxycarbonyl, alkoxy, or alkylcarbonyl, being the same or different, $R_3$ is hydrogen, and -$X_1$-Het taken together is a moiety of formula II wherein $R_4$, $R_5$, and $R_6$, being the same or different, are (a) hydrogen, (b) methyl, (c) methoxy, (d) ethoxy, (e) methoxyethoxy, or (f) ethoxyethoxy, with the provisos that (1) $R_3$, $R_4$, and $R_5$ are not all hydrogen, and (2) two of $R_3$, $R_4$, and $R_5$ are hydrogen only when the third is not methyl, and wherein $R_7$ is hydrogen, methyl, or ethyl; and the pharmacologically acceptable salts thereof.

Most especially included in the scope of said cytoprotective heterocyclylalkylsulfinylbenzimidazoles are compounds selected from the group consisting of 2-[2-(3,4-dimethyl)-pyridylmethylsulfinyl]-(5-acetyl-6-methyl)-benzimidazole,
2-[2-(3,5-dimethyl)-pyridylmethylsulfinyl]-(4,6-dimethyl)-benzimidazole,
2-[2-(4,5-dimethyl)-pyridylmethylsulfinyl]-(5-carbomethoxy)-benzimidazole,
2-[2-(4,5-dimethyl)-pyridylmethylsulfinyl]-(5-acetyl-6-methyl)-benzimidazole,
2-[2-(4,5-dimethyl)-pyridylmethylsulfinyl]-(5-carbomethoxy-6-methyl)-benzimidazole,
2-[2-(3,4-dimethyl)-pyridylmethylsulfinyl]-(5-carbomethoxy-6-methyl)-benzimidazole,
2-[2-(3,5-dimethyl)-pyridylmethylsulfinyl]-(5-acetyl-6-methyl)-benzimidazole,
2-[2-(3,4,5-trimethyl)-pyridylmethylsulfinyl]-(5-acetyl-6-methyl)-benzimidazole,
2-[2-(4-methoxy)-pyridylmethylsulfinyl]-(5-acetyl-6-methyl)-benzimidazole,
2-[2-(4-methoxy)-pyridylmethylsulfinyl]-(4,6-dimethyl)-benzimidazole,
2-[2-(3,5-dimethyl-4-methoxy)-pyridylmethylsulfinyl]-(5-acetyl-6-methyl)-benzimidazole,
2-[2-(3,5-dimethyl)-pyridylmethylsulfinyl]-(5-carbomethoxy-6-methyl)-benzimidazole,
2-[2-(3,4,5-trimethyl)-pyridylmethylsulfinyl]-(5-carbomethoxy-6-methyl)-benzimidazole,
2-[2-(4-methoxy)-pyridylmethylsulfinyl]-(5-carbomethoxy-6-methyl)-benzimidazole,
2-[2-(4-ethoxy)-pyridylmethylsulfinyl]-(5-carbomethoxy-6-methyl)-benzimidazole,
2-[2-(3-methyl-4-methoxy)-pyridylmethylsulfinyl]-(5-carbomethoxy-6-methyl)-benzimidazole,
2-[2-(3,5-dimethyl-4-methoxy)-pyridylmethylsulfinyl]-(5-carbomethoxy-6-methyl)-benzimidazole,
2-[2-(4-methoxy-5-methyl)-pyridylmethylsulfinyl]-(5-carbomethoxy-6-methyl)-benzimidazole,
2-[2-(3,5-dimethyl)-pyridylmethylsulfinyl]-(5-carbomethoxy)-benzimidazole,
2-[2-(3,5-dimethyl-4-methoxy)-pyridylmethylsulfinyl]-(5-carbomethoxy)-benzimidazole,
2-[2-(3,5-dimethyl-4-methoxy)-pyridylmethylsulfinyl]-(5-acetyl)-benzimidazole,
2-[2-(4-methoxy-5-methyl)-pyridylmethylsulfinyl]-(5-methoxy)-benzimidazole,
2-[2-(3,5-dimethyl-4-methoxy)-pyridylmethylsulfinyl]-(5-methoxy)-benzimidazole,
2-[2-(3,5-dimethyl-4-methoxy)-pyridylmethylsulfinyl]-(5-methyl)-benzimidazole,
2-[2-(3,5-dimethyl-4-methoxy)-pyridylmethylsulfinyl]-benzimidazole, or
2-[2-(3,5-dimethyl-4-methoxy)-pyridylmethylsulfinyl]-(5-chloro)-benzimidazole.

Also included within the scope of said cytoprotective heterocyclylalkylsulfinylbenzimidazoles are compounds selected from the group 2-[2-pyridylmethylsulfinyl]benzimidazole [i.e., timoprazole],
2-[2-pyridylmethylsulfinyl]-(4,6-dimethyl)benzimidazole,
2-[2-pyridylmethylsulfinyl]-(5-ethyl)benzimidazole,
2-[2-pyridylmethylsulfinyl]-(4-methyl,6-chloro)benzimidazole,
2-[2-pyridylmethylsulfinyl]-(5-methoxy)benzimidazole,
2-[2-pyridylmethylsulfinyl]-(5-hydroxy)benzimidazole,
2-[2-pyridiylmethylsulfinyl]-(5-acetyl)benzimidazole,
2-[2-pyridylmethylsulfinyl]-(5-carboxy)benzimidazole,
2-[2-pyridylmethylsulfinyl]-(5-carbethoxy)benzimidazole,
2-[2-(4-chloro)pyridylmethylsulfinyl]benzimidazole,
2-[2-(5-methyl)pyridylmethylsulfinyl]benzimidazole,
2-[2-pyridylmethylsulfinyl]-N-methylbenzimidazole,
2-[2-pyridyl-(methyl)methylsulfinyl]benzimidazole,
2-[2-pyridylmethylsulfinyl]-(4-methyl)benzimidazole,
2-[2-pyridylmethylsulfinyl]-(N-acetyl)benzimidazole,
2-[2-pyridylmethylsulfinyl]-(N-methoxycarbonyl)benzimidazole,
2-[2-pyridylmethylsulfinyl]-(5-methyl)benzimidazole,
2-[2-pyridylmethylsulfinyl]-(5-chloro)benzimidazole,
2-[2-pyridylmethylsulfinyl]-(5-isopropyl)benzimidazole,
2-[2-pyridylmethylsulfinyl]-(5-t-butyl)benzimidazole,
2-[2-pyridylmethylsulfinyl]-(5-n-propyl)benzimidazole,
2-[2-pyridylmethylsulfinyl]-(N-carbamoyl)benzimidazole,
2-[2-pyridylmethylsulfinyl]-(N-methylcarbamoyl)benzimidazole,
2-[2-pyridylmethylsulfinyl]-(N-acetylmethyl)benzimidazole,
2-[2-pyridylmethylsulfinyl]-(N-ethoxycarbonylmethyl)benzimidazole,
2-[2-pyridylmethylsulfinyl]-(N-methylsulfonyl)benzimidazole,
2-[2-(4-methyl)pyridylmethylsulfinyl]-(5-methyl)benzimidazole,
2-[2-(5-methyl)pyridylmethylsulfinyl]-(5-methyl)benzimidazole,
2-[2-pyridylmethylsulfinyl]-(6-chloro)benzimidazole,
2-[2-pyridyl-(ethyl)methylsulfinyl]benzimidazole,
2-[2-pyridyl-(ethyl)methylsulfinyl]-(5-chloro)benzimidazole,
2-[2-pyridyl-(methyl)methyllsulfinyl]-(5-ethyl)benzimidazole,
2-[2-(3-methyl)pyridylmethylsulfinyl]benzimidazole,
2-[2-(5-ethyl)pyridylmethylsulfinyl]-(5-methyl)benzimidazole,
2-[2-(5-ethyl)pyridylmethylsulfinyl]benzimidazole,
2-[2-pyridyl-(ethyl)methylsulfinyl]-(5-ethyl)benzimidazole, 2-[2-pyridyl-(methyl)methylsulfinyl]-(5-cyano)benzimidazole, 2-[2-pyridyl-(methyl)methylsulfinyl]-(5-trifluoromethyl)benzimidazole, 2-[2-pyridyl-(ethyl)methylsulfinyl]-(5-methyl)benzimidazole, 2-[2-pyridyl-(ethyl)methylsulfinyl]-(5-cyano)benzimidazole, 2-[2-pyridyl-(ethyl)methylsulfinyl]-(5-trifluoromethyl)benzimidazole, 2-[2-pyridylmethylsulfinyl]-(4-chloro)benzimidazole, 2-[2-pyridyl-(isopropyl)methylsulfinyl]benzimidazole, 2-[2-pyridyl-(methyl)methylsulfinyl]-(5,6-dimethyl)benzimidazole, and 2-[2-pyridylmethylsulfinyl]-(5,6-dimethyl)benzimidazole.

The present invention in part relates to compositions and methods for treatment of non-gastric-acid-induced, non-traumatically-induced, non-neoplastic gastrointestinal inflammatory diseases. This term of art is used in its ordinary and conventional sense, such as U.S. Pat. No. 4,083,998, cited above.

Mammals suffering from these inflammatory diseases are readily diagnosed by an attending physician or veterinarian of ordinary skill in the art. Mammals particularly susceptible to the development of these diseases are those mammals whose environment or medical history provides a known predisposition to gastrointestinal inflammatory disease. For example, mammals especially susceptible to gastric inflammatory diseases include those:

(1) with a history of multiple episodes of gastric or duodenal ulceration, (2) with a history of chronic and excessive ethanol consumption, (3) with a recent acute exposure to a cytodestructive dose of ionizing radiation, (4) with an acute or chronic ingestive exposure to cytodestructive chemical agents, including cytodestructive chemical agents, or (5) with a recent exposure to pathogens capable of producing cytodestructive conditions. Similarly, those mammals with a history of colitis, especially ulcerative colitis, are likewise known in the art to be particularly susceptible to recurrence of this gastrointestinal inflammatory disease.

Mammals to whom the cytoprotective heterocyclylalkylsulfinylbenzimidazoles are administered are particularly and especially humans, although other valuable domestic animals and experimental animals are also included within the scope of the present invention.

In accordance with the novel methods employing these cytoprotective heterocyclylalkylsulfinylbenzimidazoles, the present invention provides for oral administration. Accordingly, oral administration described in Appendix A and U.S. Pat. No. 4,045,563 is conveniently employed.

Appropriate oral pharmaceutical compositions are formulated for use in accordance with the present invention. Such pharmaceutical compositions are employed as described in U.S. Pat. No. 4,045,563, incorporated by reference, and Appendix A, except that in place of an antisecretory amount of the heterocyclylalkylsulfinylbenzimidazole, a cytoprotective amount, i.e., an amount effective to treat or prevent the non-traumatically-induced, non-neoplastic gastrointestinal inflammatory disease, is employed in the composition.

Particularly and especially, the compositions employed in accordance with the present invention are in a unit dosage form, as that term is employed in the art, and contain in the unit dosage an amount of the cytoprotective heterocyclylalkylsulfinylbenzimidazole which is both effective to treat or prevent the gastric inflammatory disease and less than the gastric antisecretory $ED_{50}$ (dose effective to inhibit 50% of basal acid secretion) of the cytoprotective heterocyclylalkylsulfinylbenzamidizole. Hence these compositions, which by definition provide insubstantial gastric antisecretory effects, are nonetheless surprisingly nd unexpectedly effective as cytoprotective pharmaceutical compositions.

The amount of the cytoprotective heterocyclylalkylsulfinylbenzimidazole effective to treat or prevent the gastrointestinal inflammatory diseases is an amount which varies according to the mammal being treated, the severity of the disease, the route of administration selected, and the particular heterocyclylalkylsulfinylbenzimidazole being employed. Ordinarily, the relative potencies of these cytoprotective heterocyclylalkylsulfinylbenzimidazoles are determined by tests in standard laboratory animals described in Example 1 and employed in accordance with the present method in proportion to their relative potencies. Accordingly, such determinations are readily within the skill of pharmacologists in the art.

These cytoprotective heterocyclylalkylsulfinylbenzimidazoles are accordingly administered one to 6 times daily at dosages between from about 0.1 μg to about 100 mg/kg/day orally.

Prevention of the gastrointestinal inflammatory diseases results in the reduction of the incidence and severity of ulceration ordinarily produced by the disease, including total prevention of the inflammatory process. Treatment results in accelerated and more complete and satisfactory healing of ulcers and other manifestations of the inflammatory process. Accordingly the present invention provides a surprisingly and unexpectedly valuable means of treating gastrointestinal disease than was heretofore available with heterocyclylalkylsulfinylbenzimidazoles and provides for the pharmacological use of these compounds at lower effective doses than heretofore possible.

DESCRIPTION OF THE PREFERRED EMBODIMENTS

EXAMPLE 1 Effect of timoprazole, 2-[2-pyridylmethylsulfinyl]benzimidazole, on ethanol-induced gastric lesions A. Four groups of rats, standard laboratory animals for determining cytoprotective effects of pharmacological agents, are fasted for 24 hr and then treated orally with (a) trimoprazole, (b) cimetidine, (c) a cytoprotective prostaglandin, or (d) vehicle (10% Emulphor, 10% EtOH, 80% water). Thirty min later, the rats are challenged with an oral 1 ml dose of 80% aqueous ethanol, a standard agent for inducing gastric cytodestruction. One hr later, the rats are sacrificed (carbon dioxide asphyxiation) and the gastric tissues examined. Rats treated with timoprazole at 0.3, 1, 3, or 10 mg/kg demonstrate no gastric ulceration. Rats treated with a dose of 0.3 mg/kg show traces of mild ulceration. In contrast, rats treated with cimetidine at 0.3, 1.0, 3.0 or 10.0 mg/kg all demonstrate gastric ulcers, although a slight decrease in the number of ulcers is noted. Timoprazole has ED$_{50}$ for gastric acid secretion inhibition of approximately 10 mg/kg in the rat, at least ten times greater than the lowest cytoprotective dose observed in the experiment.

B. A further experiment is undertaken to rule out gastric emptying as a factor in the cytoprotection observed in part A above. In this experiment timoprazole was given orally at 0.01, 0.1, or 1.0 mg/kg to groups of rats and a further group of rats is treated with vehicle (same as in part A) only. As above, the rats are faster for 24 hr prior to treatment. Groups of rats are then sacrificed 5, 15, and 30 min after timoprazole ingestion. No significant changes in gastric volume between rats treated with vehicle and rats treated with timoprazole is observed at any of the three sacrifice times. Accordingly, flluid accumulation in the stomach is not a factor in the cytoprotection observed in part A.

C. A further experiment is performed to determine the lowest dose of timoprazole at which 50% of the animals treated exhibit no gastric ulceration (ED$_{50}$), employing a vehicle with less "mild irritant" effects than in part A. Groups of rats are fasted for 24 hr and then treated orally or subcutaneously with timoprazole at 1, 3, or 10 mg/kg in vehicle (5% EtOH, 1% Emulphor in water) at 30 min before ethanol challenge. The rats are sacrificed one hr after timoprazole administration and the extent of gastric ulceration determined. Subcutaneous administration of timoprazole did not significantly reduce the number of ulcers compared to control (vehicle-treated) rats. Oral administration produced a significant reduction in ulceration at all dosages tested and the ED$_{50}$ is determined to be below 1 mg/kg.

D. Because mild gastric irritants, e.g., 20% ethanol, are known to stimulate endogenous prostaglandin production, with consequent cytoprotection effects being observed, a further experiment is undertaken to determine whether timoprazole acts as a mild irritant (i.e., by stimulating endogenous cytoprotective prostaglandin production), or exerts a directly cytoprotective effect. In this experiment, rats are treated with timoprazole (5 mg/kg orally), but in each group of rats half the animals are pretreated with a NOSAC, indomethacin, 1 hr prior to treatment with timoprazole. One hr after ethanol challenge, the rats are sacrificed. However, no significant difference is observed between rats receiving indomethicin and those not receiving indomethicin. Accordingly, the cytoprotective effects of timoprazole are not mediated by endogenous prostaglandin production.

EXAMPLE 2 Cytoprotective effect of timoprazole against thermally induced gastric ulceration Following the procedure of Example 1, but employing boiling water (greater than 85°–95° C.) in place of 80% ethanol, there is obtained a uniform reduction in the incidence and severity of ulcers in timoprazole-treated rats (0.3, 1.0, 3.0, and 10.0 mg/kg) as compared to rats receiving vehicle only. Using the ulcer incidence (ulcers/stocmach) scoring system of Robert (U.S. Pat. No. 4,097,603, column 4, lines 41–53), the control group exhibits a score of 8.0, while the treated group exhibits a scores of 7.6 (0.3 mg/kg), 5.0 (1.0 mg/kg), 3.9 (3.0 mg/kg), and 4.0 (10.0 mg/kg).

FORMULAS

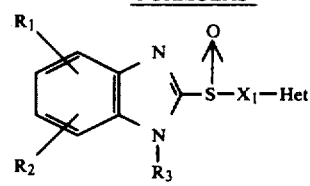

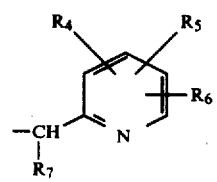

APPENDIX A

Substituted pyridylsulfinylbenzimidazoles having gastric acid secretion properties, pharmaceutical preparations containing same, and intermediates for their preparation The present invention relates to new compounds having valuable properties in affecting gastric acid secretion in mammals, including man, as well as the process for their preparation, method of affecting gastric acid secretion and pharmacetical preparations containing said novel compounds.

The object of the present invention is to obtain compounds which affect gastric acid secretion, and which inhibit exogenously or endogenously stimulated gastric acid secretion. These compounds can be used in the treatment of peptic ulcer disease.

It is previously known that compounds of the formulas I and II

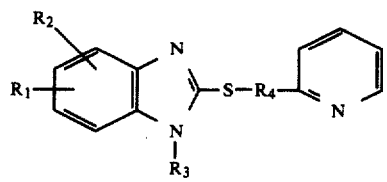

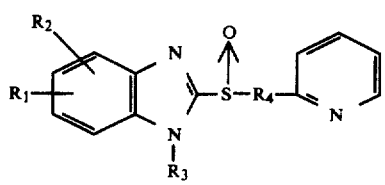

wherein $R_1$ and $R_2$ are each selected from the group consisting of hydrogen, alkyl, halogen, cyano, carboxy, carboxyalkyl, carboalkoxy, carboalkoxyalkyl, carbamoyl, carbamoyloxy, hydroxy, alkoxy, hydroxyalkyl, trifluoromethyl and acyl in any position. $R_3$ is selected from the group consisting of hydrogen, alkyl, acyl, carboalkoxy, carbamoyl, alkylcarbamoyl, dialkylcarbamoyl, alkylcarbonylmethyl, alkoxycarbonylmethyl, and alkylsulphonyl, and $R_4$ is selected from the group consisting of straight and branched alkylene groups having 1 to 4 carbon atoms, whereby at most one methylene group is present between S and the pyridyl group, and whereby the pyridyl group may be further substituted with alkyl or halogen, possess inhibiting effect of gastric acid secretion.

It has now, however, surprisingly been found that the compounds defined below possess a still greater inhibiting effect than those given above.

Compounds of the invention are those of the general formula III

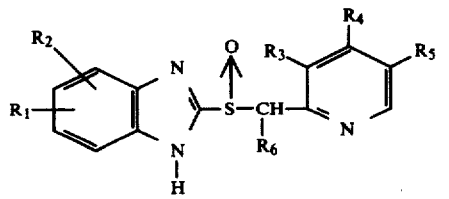

wherein $R_1$ and $R_2$ are same or different and are each selected from the group consisting of hydrogen, alkyl, halogen, carbomethoxy, carbethoxy, alkoxy, and alkanoyl. $R_6$ is selected from the group consisting of hydrogen, methyl, and ethyl, and $R_3$, $R_4$ and $R_5$ are same or different and are each selected from the group consisting of hydrogen, methyl, methoxy, ethoxy, methoxyethoxy and ethoxyethoxy wherein $R_3$, $R_4$, and $R_5$ are not all hydrogen, and whereby when two of $R_3$, $R_4$, and $R_5$ are hydrogen, the third of $R_3$, $R_4$ and $R_5$ is not methyl.

Alkyl $R_1$ and $R_2$ of formula III are suitably alkyl having up to 7 carbon atoms, preferably up to 4 carbon atoms. Thus, alkyl R may be methyl, ethyl, n-propyl, isopropyl, n-butyl or isobutyl.

Halogen $R_1$ and $R_2$ is chloro, bromo, fluoro, or iodo.

Alkoxy $R_1$ and $R_2$ are suitably alkoxy groups having up to 5 carbon atoms, preferably up to 3 carbon atoms, as methoxy, ethoxy, n-propoxy, or isopropoxy.

Alkanoyl $R_1$ and $R_2$ have preferably up to 4 carbon atoms and are e.g. formyl, acetyl, or propionyl, preferably acetyl.

A preferred group of compounds of the general formula III are those wherein $R_1$ and $R_2$ are the same or different and are each selected from the group consisting of hydrogen, alkyl, carbomethoxy, alkoxy, and alkanoyl, wherein $R_1$ and $R_2$ are not both hydrogen, $R_6$ is hydrogen, and $R_3$, $R_4$, and $R_5$ are the same or different and are each selected from the group consisting of hydrogen, methyl, methoxy, and ethoxy, wherein $R_3$, $R_4$, and $R_5$ are not all hydrogen, and whereby when two of $R_3$, $R_4$, and $R_5$ are not all hydrogen, and whereby when two of $R_3$, $R_4$, and $R_5$ are hydrogen the third of $R_3$, $R_4$, and $R_5$ is not methyl.

A second preferred group of compounds of the general formula III are those wherein $R_1$ and $R_2$ are the same or different and are each selected from the group consisting of hydrogen, alkyl, halogen, carbomethoxy, carbethoxy, alkoxy, and alkanoyl, $R_6$ is selected from the group consisting of hydrogen, methyl, and ethyl, $R_3$ is methyl, $R_4$ is methoxy, and $R_5$ is methyl.

A third preferred group of compounds of the general formula III are those wherein $R_1$ and $R_2$ are the same or different and are each selected from the group consisting of hydrogen, alkyl, halogen, carbomethoxy, carbethoxy, alkoxy and alkanoyl, $R_6$ is selected from the group consisting of hydrogen, methyl and ethyl, and $R_3$ is hydrogen, $R_4$ is methoxy and $R_5$ is methyl or $R_3$ is methyl, $R_4$ is methoxy and $R_5$ is hydrogen.

A fourth preferred group of compounds of the general formula III are those wherein $R_1$ and $R_2$ are the same or different and are each selected from the group consisting of hydrogen, alkyl, halogen, carbomethoxy, carbethoxy, alkoxy, and alkanoyl, $R_6$ is selected form the group consisting of hydrogen, methyl and ethyl, $R_3$ and $R_5$ are hydrogen and $R_4$ is methoxy.

A fifth preferred group of compounds of the general formula III are those wherein $R_1$ and $R_2$ are the same or different and are each selected from the group consisting of hydrogen, alkyl, halogen, carbomethoxy, carbethoxy, alkoxy, and alkanoyl, $R_6$ is selected from the group consisting of hydrogen, methyl and ethyl, and $R_3$ and $R_5$ are methyl and $R_4$ is hydrogen.

A sixth preferred group of compounds of the general formula III are those wherein $R_1$ and $R_2$ are the same or different and are each selected from the group consisting of hydrogen, alkyl, halogen, carbomethoxy, carbethoxy, alkoxy, and alkanoyl, $R_6$ is selected from the group consisting of hydrogen, methyl and ethyl, $R_3$ and $R_5$ are hydrogen and $R_4$ is ethoxy, methoxyethoxy or ethoxyethoxy.

A seventh preferred group of compounds of the general formula III are those wherein $R_1$ and $R_2$ are the same or different and are each selected from the group consisting of hydrogen, alkyl, halogen, carbomethoxy, alkoxy, and alkanoyl, $R_6$ is selected from the group consisting of hydrogen, methyl, and ethyl, $R_3$, $R_4$, and $R_5$ are all methyl.

Compounds of formula III above may be prepared according to the following methods:

(a) oxidizing a compound of formula IV

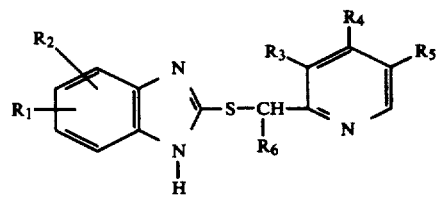

wherein $R_1$, $R_2$, $R_6$, $R_3$, $R_4$, and $R_5$ have the meanings given, to the formation of a compound of formula III.

(b) reacting a compound of the formula V

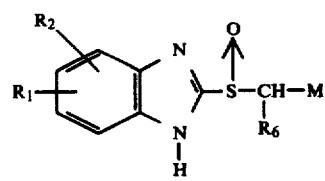

wherein $R_1$, $R_2$, and $R_6$ have the meanings given above and M is a metal selected from the group consisting of K, Na and Li, with a compound of formula VI.

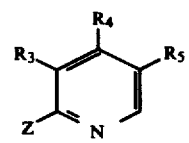

wherein $R_3$, $R_4$, and $R_5$ have the same meanings as given above, Z is a reactive esterified hydroxy group, to the formation of a compound of formula III;

(c) reacting a compound of the formula VII

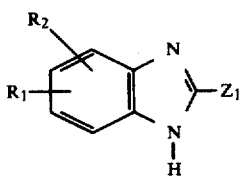

wherein $R_1$, and $R_2$ have the same meanings as given above and $Z_1$ is SH or a reactive esterified hydroxy group, with a compound of the formula VIII

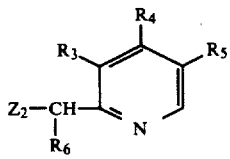

wherein $R_6$, $R_3$, $R_4$, and $R_5$ have the same meanings as given above, and $Z_2$ is a reactive esterified hydroxy group or SH, to the formation of an intermediate of formula IV above, which then is oxidized to give a compound of formula III;

(d) reacting a compound of the formula IX

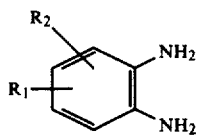

wherein $R_1$ and $R_2$ have the same meanings as given above with a compound of the formula X

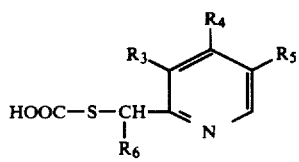

wherein $R_6$, $R_3$, $R_4$, and $R_5$ have the same meanings as given above, to the formation of an intermediate of formula IV above, which then is oxidized to give a compound of formula III, which compound may be converted to its therapeutically acceptable salts, if so desired.

In the reactions above, Z, $Z_1$, and $Z_2$ may be a reactive, esterified hydroxy group which is a hydroxy group esterified with strong, inorganic or organic acid preferably a hydrohalogen acid, such as hydrochloric acid, hydrobromic acid, or hydroiodic acid, also sulfuric acid or a strong organic sulfonic acid as a strong aromatic acid, e.g., benzenesulfonic acid, 4-bromobenzenesulfonic acid or 4-toluenesulfonic acid.

The oxidation of the sulfur atom in the chains above to sulfinyl (S→O) takes place in the presence of an oxidizing agent selected from the group consisting of nitric acid, hydrogen peroxide, peracids, peresters, ozone, dinitrogentetraoxide, iodosobenzene, N-halosuccinimide, 1-chlorobenzotriazole, t-butylhypochlorite, diazobicyclo-[2,2,2]octane bromine complex, sodium metaperiodate, selenium dioxide, manganese dioxide, chromic acid, cericammonium nitrate, bromine, chlorine, and sulfuryl chloride. The oxidation usually takes place in a solvent wherein the oxidizing agent is present in some excess in relation to the product to be oxidized.

Depending on the process conditions and the starting materials, the end product is obtained either as the free base or in the acid addition salt, both of which are included within the scope of the invention. Thus, basic, neutral or mixed salts may be obtained as well as hemi, mono, sesqui or polyhydrates. The acid addition salts of the new compounds may in a manner known per se be transformed into free base using basic agents such as alkali or by ion exchange. On the other hand, the free bases obtained may form salts with organic or inorganic acids. In the preparation of acid addition salts preferably such acids are used which form suitable therapeutically acceptable salts. Such acids include hydrohalogen acids, sulfonic, phosphoric, nitric, and perchloric acids; aliphatic, alicyclic, aromatic, heterocyclic carboxy or sulfonic acids, such as formic, acetic, propionic, succinic, glycolic, lactic, malic, tartaric, citric, ascorbic, maleic, hydroxymaleic, pyruvic, phenylacetic, benzoic, p-aminobenzoic, antranilic, p-hydroxybenzoic, salicylic or p-aminosalicylic acid, embonic, methanesulfonic, ethanesulfonic, hydroxyethanesulfonic, ethylenesulfonic, halogenbenzenesulfonic, toluenesulfonic, naphthylsulfonic or sulfanilic acids; methionine, tryptophane, lysine or arginine.

These or other salts of the new compounds, as e.g. picrates, may serve as purifying agents of the free bases obtained. Salts of the bases may be formed, separated from solutions, and then the free base can be recovered from a new salt solution in a purer state. Because of the relationship between the new compounds in free base form and their salts, it will be understood that the corresponding salts are included within the scope of the invention.

Some of the new compounds may, depending on the choice of starting materials and process, be present as optical isomers or racemate, or if they contain at least two asymmetric carbon atoms, be present as an isomer mixture (racemate mixture).

The isomer mixtures (racemate mixtures) obtained may be separated into two stereoisomeric (diastereomeric) pure racemates by means of chromatography or fractional crystal or polyhydrates. The acid addition salts of the new compounds may in a manner known per se be transformed into free base using basic agents such as alkali or by ion exchange. On the other hand, the free bases obtained may form salts with organic or inorganic acids. In the preparation of acid addition salts preferably such acids are used which form suitable therapeutically acceptable salts. Such acids include hydrohalogen acids, sulfonic, phosphoric, nitric, and perchloric acids; aliphatic, alicyclic, aromatic, heterocyclic carboxy or sulfonic acids, such as formic, acetic, propionic, succinic, glycolic, lactic, malic, tartaric, citric, ascorbic, maleic, hydroxymaleic, pyruvic, phenylacetic, benzoic, p-aminobenzoic, antranilic, p-hydroxybenzoic, salicylic or p-aminosalicylic acid, embonic, methanesulfonic, ethanesulfonic, hydroxyethanesulfonic, ethylenesulfonic, halogenbenzenesulfonic, toluenesulfonic, naphthylsulfonic or sulfanilic acids; methionine, tryptophane, lysine or arginine.

These or other salts of the new compounds, as e.g. picrates, may serve as purifying agents of the free bases obtained. Salts of the bases may be formed, separated from solution, and then the free base can be recovered from a new salt solution in a purer state. Because of the relationship between the new compounds in free base form and their salts, it will be understood that the corresponding salts are included within the scope of the invention.

Some of the new compounds may, depending on the choice of starting materials and process, be present as optical isomers or racemate, or if they contain at least two asymmetric carbon atoms, be present as an isomer mixture (racemate mixture).

The isomer mixtures (racemate mixtures) obtained may be separated into two steroisomeric (diastereomeric) pure racemates by means of chromatography or fractional crystallization.

The racemates obtained can be separated according to known methods, e.g. recrystallization from an optically active solvent, use of microorganisms, reactions with optically active acids forming salts which can be separated, separation based on different solubilities of the diastereomers. Suitable optically active acids are the L- and D-forms of tartaric acid, di-o-tolyl-tartaric acid, malic acid, mandelic acid, camphorsulfonic acid or quinic acid. Preferably the more active part of the two antipodes is isolated.

The starting materials are known or may, if they should be new, be obtained according to processes known per se.

In clinical use the compounds of the invention are administered orally, rectally or by injection in the form of a pharmaceutical preparation which contains an active component either as a free base or as a pharmaceutically acceptable, non-toxic acid addition salt, such as hydrochloride, lactate, acetate, sulfamate, in combination with a pharmaceutically acceptable carrier. The carrier may be in the form of a solid, semisolid or liquid diluent, or a capsule. These pharmaceutical preparations are a further object of the invention. Usually the amount of active compound is between 0.1 to 95% by weight of the preparation, between 0.5 to 20% by weight in preparations for injection and between 2 and 50% by weight in preparations for oral administration.

In the preparation of pharmaceutical preparations containing a compound of the present invention in the form of dosage units for oral administration the compound selected may be mixed with a solid, pulverulent carrier, such as lactose, saccharose, sorbitol, mannitol, starch, amylopectin, cellulose derivatives or gelatin, as well as with an anti-friction agent such as magnesium stearate, calcium stearate, and polyethyleneglycol waxes. The mixture is then pressed into tablets. If coated tablets are desired, the above prepared core may be coated with a concentrated solution of sugar, which may contain gum arabic, gelatin, talc, titanium dioxide or with a lacquer dissolved in volatile organic solvent or mixture of solvents. To this coating various dyes may be added in order to distinguish among tablets with different active compounds or with different amounts of the active compound present.

Soft gelatin capsules may be prepared which capsules contain a mixture of the active compound or compounds of the invention and vegetable oil. Hard gelatin capsules may contain granules of the active compound in combination with a solid, pulverulent carrier as lactose, saccharose, sorbitol, mannitol, potato starch, corn starch, amylopectin, cellulose derivatives of gelatin.

Dosage units for rectal administration may be prepared in the form of suppositories which contain the active substance in a mixture with a neutral fat base, or they may be prepared in the form of gelatin-rectal capsules which contain the active substance in a mixture with a vegetable oil or paraffin oil.

Liquid preparations for oral administration may be prepared in the form of syrups or suspensions, e.g. solutions containing from 0.2% to 20% by weight of the active ingredient and the remainder consisting of sugar and a mixture of ethanol, water, glycerol and propylene glycol. If desired, such liquid preparations may contain colouring agents, flavouring agents, saccharin and carboxymethyl-cellulose as a thickening agent.

Solutions for parenteral administration by injection may be prepared as an aqueous solution of a watersoluble pharmaceutically acceptable salt of the active compound, preferably in a concentration from 0.5% to 10% by weight. These solutions may also contain stabilizing agents and/or buffering agents and may be manufactured in different dosage unit ampoules.

Pharmaceutical tablets for oral use are prepared in the following manner: The solid substances are ground or sieved to a certain particle size, and the binding agent is homogenized and suspended in a suitable solvent. The therapeutically active compounds and auxiliary agents are mixed with the binding agent solution. The resulting mixture is moistened to form a uniform suspension having the consistency of wet snow. The moistening causes the particles to aggregate slightly, and the resulting mass is pressed through a stainless steel sieve having a mesh size of approximately 1 mm. The layers of the mixture are dried in carefully controlled drying cabinets for approximately ten hours to obtain the desired particle size and consistency. The granules of the dried mixture are sieved to remove any powder. To this mixture, disintegrating, anti antifriction and antiadhesive agents are added. Finally, the mixture is pressed into tablets using a machine with the appropriate punches and dies to obtain the desired tablet size. The pressure applied affects the size of the tablet, its strength and its ability to dissolve in water. The compression pressure used should be in the range 0.5 to 5 tons. Tablets are manufactured at the rate of 20.000 to 200.000 per hour. The tablets, especially those which are rough or bitter, may be coated with a layer of sugar or some other palatable substance. They are then packaged by machines having electronic counting devices. The different types of packages consist of glass or plastic gallipots, boxes, tubes and specific dosage adapted packages.

The typical daily dose of the active substance varies according to the individual needs and the manner of administration. In general, oral dosages range from 100 to 400 mg/day of active substance and intravenous dosages range from 5 to 20 mg/day.

The following illustrates a preferred embodiment of the invention without being limited thereto. Temperature is given in degrees Centigrade.

The starting materials in the examples found below were prepared in accordance with the following methods: (1) a 1,2-diamino compound, such as o-phenylenediamine was reacted with potassium ethylxanthate (according to Org. Synth. Vol. 30, p. 56) to form a 2-mercaptobenzimidazole; (2) the compound 2-chloromethylpyridine was prepared by reacting 2-hydroxymethylpyridine with thionylchloride (according to Arch. Pharm. Vol. 26, pp. 448–451 (1956)); (3) the compound 2-chloromethylbenzimidazole was prepared by condensing o-phenylenediamine with chloroacetic acid.

EXAMPLE 1

28.9 g of 2-[2-(4,5-dimethyl)pyridylmethylthio]-(5-acetyl-6-methyl)-benzimidazole were dissolved in 160 ml of CHCl$_3$, 24.4 g of m-chloroperbenzoic acid were added in portions while stirring and cooling to 5° C. After 10 minutes, the precipitated m-chlorobenzoic acid was filtered off. The filtrate was diluted with CH$_2$Cl$_2$, washed with Na$_2$CO$_3$ solution, dried over Na$_2$SO$_4$ and evaporated in vacuo. The residue crystallized when diluted with CH$_3$CN, and 2-[2-(4,5-dimethyl)pyridylmethylsulfinyl]-(5-acetyl-6-methyl)benzimidazole was recrystallized from CH$_3$CN. Yield 22.3 g; m.p. 158° C.

EXAMPLES 2–30

The preparation of compounds of formula III labelled 2–26 was carried out in accordance with Example 1 above. The compounds prepared are listed in Table 1 which identifies the substituents for these compounds.

EXAMPLE 31 (METHOD C)

0.1 moles of 4-6-dimethyl-2-mercaptobenzimidazole were dissolved in 20 ml of water and 200 ml of ethanol containing 0.2 moles of sodium hydroxide. 0.1 moles of 2-chloro-methyl-(3,5-dimethyl)pyridine hydrochloride were added and the mixture was refluxed for two hours. The sodium chloride formed was filtered off and the solution was evaporated in vacuo. The residue was dissolved in acetone and was treated with active carbon. An equivalent amount of concentrated hydrochloric acid was added, whereupon the mono-hydrochloride of 2-[2-(3,5-dimethyl)pyridylmethylthio]-(4,6-dimethyl)benzimidazole was isolated. Yield 0.05 moles.

This compound was then oxidized in accordance with Example 1 above to give the corresponding sulfinyl compound melting point 50°–55° C.

EXAMPLE 32 (METHOD B)

0.1 moles of 2-[Li-methylsulfinyl](5-acetyl-6-methyl)-benzimidazole were dissolved in 150 mls of benzene. 0.1 moles of 2-chloro-(3,5-dimethyl)pyridine were added and the mixture was refluxed for two hours. The lithiumchloride formed was filtered off, and the solution was evaporated in vacuo. The residue was crystallized from CH$_3$CN, and recrystallized from the same solvent. Yield 0.82 moles of 2-[2-(3,5-dimethyl)pyridylmethylsulfinyl]-(5-acetyl-6-methyl)benzimidazole melting at 171° C.

EXAMPLE 33 (METHOD D)

23.4 g of 2-[2-(3,4,5-trimethyl)pyridylmethylthio] formic acid and 16.6 g of o-(5-acetyl-6-methyl)-phenylenediamine were boiled for 40 minutes in 100 ml of 4 N HCl. The mixture was cooled and neutralized with ammonia. The neutral solution was then extracted with ethyl acetate. The organic phase was treated with active carbon and evaporated in vacuo. The residue was dissolved in acetone whereupon an equivalent of concentrated HCl was added. The precipitated hydrochloride was filtered off after cooling and the salt was recrystallized from absolute ethanol and some ether. Yield of 2-[2-(3,4,5-trimethylpyridyl)methylthio]-(5-acetyl-6-methyl)benzimidazole was 6.5 g.

This compound was then oxidized in accordance with Example 1 above, to give the corresponding sulfinyl derivative. M.p. 190° C.

EXAMPLE 34 (METHOD C)

22.0 g of 2-mercapto-(5-acetyl-6-methyl)benzimidazole and 19.5 g of chloromethyl(4,5-dimethyl)-pyridine hydrochloride were dissolved in 200 ml of 95% ethanol. 8 g of sodium hydroxide in 20 ml of water were added, whereupon the solution was refluxed for two hours. The sodium chloride formed was filtered off and the solution was evaporated in vacuo. The residue, 2-[2-(4,5-dimethyl)pyridylmethylthio]-(5-acetyl-6-methyl)benzimidazole, was recrystallized from 70% ethanol. Yield 10.6 g.

This compound was then oxidized in accordance with Example 1 above, to give the corresponding sulfinyl derivative. M.p. 158° C.

TABLE 1

| Ex | R$_1$ | R$_2$ | R$_6$ | R$_3$ | R$_4$ | R$_5$ | M.p. °C. |
|----|-------|-------|-------|-------|-------|-------|----------|
| 1  | 5-COCH$_3$   | 6-CH$_3$ | H | H   | CH$_3$  | CH$_3$ | 158 |
| 2  | 5-COOCH$_3$  | 6-CH$_3$ | H | H   | CH$_3$  | CH$_3$ | 163 |
| 3  | 5-COOCH$_3$  | H        | H | H   | CH$_3$  | CH$_3$ | 141 |
| 4  | 5-COCH$_3$   | 6-CH$_3$ | H | CH$_3$ | CH$_3$ | H      | 160 |
| 5  | 5-COOCH$_3$  | 6-CH$_3$ | H | CH$_3$ | CH$_3$ | H      | 163 |
| 6  | 4-CH$_3$     | 6-CH$_3$ | H | CH$_3$ | H      | CH$_3$ | 50–55 |
| 7  | 5-COCH$_3$   | 6-CH$_3$ | H | CH$_3$ | H      | CH$_3$ | 171 |
| 8  | 5-COCH$_3$   | 6-CH$_3$ | H | CH$_3$ | CH$_3$ | CH$_3$ | 190 |
| 9  | 5-COCH$_3$   | 6-CH$_3$ | H | H      | OCH$_3$| H      | 165 |
| 10 | 4-CH$_3$     | 6-CH$_3$ | H | H      | OCH$_3$| H      | 122 |
| 11 | 5-COCH$_3$   | 6-CH$_3$ | H | CH$_3$ | COH$_3$| CH$_3$ | 156 |
| 12 | 5-COOCH$_3$  | 6-CH$_3$ | H | CH$_3$ | H      | CH$_3$ | 144 |
| 13 | 5-COOCH$_3$  | 6-CH$_3$ | H | CH$_3$ | CH$_3$ | CH$_3$ | 185 |
| 14 | 5-COOCH$_3$  | 6-CH$_3$ | H | H      | OCH$_3$| H      | 169 |
| 15 | 5-COOCH$_3$  | 6-CH$_3$ | H | H      | OC$_2$H$_5$ | H | 148 |
| 16 | 5-COOCH$_3$  | 6-CH$_3$ | H | CH$_3$ | OCH$_3$| H      | 175 |
| 17 | 5-COOCH$_3$  | 6-CH$_3$ | H | CH$_3$ | OCH$_3$| CH$_3$ | 155 |
| 18 | 5-COOCH$_3$  | 6-CH$_3$ | H | H      | OCH$_3$| CH$_3$ | 158 |
| 19 | 5-COOCH$_3$  | H        | H | CH$_3$ | H      | CH$_3$ | 141 |
| 20 | 5-COOCH$_3$  | H        | H | CH$_3$ | OCH$_3$| CH$_3$ | 142 |
| 21 | 5-COCH$_3$   | H        | H | CH$_3$ | OCH$_3$| CH$_3$ | 162 |
| 22 | 5-OCH$_3$    | H        | H | H      | OCH$_3$| CH$_3$ | 178 |
| 23 | 5-OCH$_3$    | H        | H | CH$_3$ | OCH$_3$| CH$_3$ | 156 |
| 24 | 5-CH$_3$     | H        | H | CH$_3$ | OCH$_3$| CH$_3$ | 181 |
| 25 | H            | H        | H | CH$_3$ | OCH$_3$| CH$_3$ | 165 |
| 26 | 5-Cl         | H        | H | CH$_3$ | OCH$_3$| CH$_3$ | 185 |
| 27 | 5-CH$_3$     | H        | H | H      | OC$_2$H$_4$OCH$_3$ | H | 119 |
| 28 | 5-COOC$_2$H$_5$ | H     | H | CH$_3$ | OCH$_3$| CH$_3$ | 150–5 |
| 29 | 5-COOCH$_3$  | H        | CH$_3$ | CH$_3$ | H  | CH$_3$ | 130 |
| 30 | 5-CH$_3$     | H        | CH$_3$ | CH$_3$ | H  | CH$_3$ | 152 |

BIOLOGICAL EFFECT

The compounds of the invention possess worthwhile therapeutic properties as gastric acid secretion inhibitors as demonstrated by the following tests. To determine the gastric acid secretion inhibitory properties, experiments have been performed on conscious dogs provided with gastric fistulas of conventional type and duodenal fistules, the latter ones used for direct introduodenal administration of the test compounds. After 18 hours starvation and deprivation of water the dogs were given subcutaneous infusion of pentagastrin (1–4 nmol/kg, h) lasting for 6–7 hours. Gastric juice was collected in consecutive 30 minutes samples. An aliquot of each sample was titrated with 0.1 N NaOH to pH 70 for titrable acid concentration using an automatic titrator and pH-meter (Radiometer, Copenhagen, Denmark). Acid output was calculated as mmol $H^+/60$ minutes. The percent inhibition compared to control experiments was calculated for each compound and the peak inhibitory effect is given in Table 2 below. The test compounds, suspended in 0.5% Methocel ® (methyl cellulose), were given intraduodenally in doses from 4–20 μmol/kg when the secretory response to pentagastrin has reached a steady level.

In the test prior known compounds were compared with the compounds of the present invention as will be evident from the Table 2 below.

The following gastric acid inhibiting effect data were obtained for a number of compounds tested according to the method described.

EXAMPLE 35

A syrup containing 2% (weight per volume) of active substance was prepared from the following ingredients:

| | |
|---|---|
| 2-[2-(4,5-dimethyl)-pyridylmethylsulfinyl]-(5-acetyl-6-methyl)benzimidazole.HCl | 2.0 g |
| Sugar | 0.6 g |
| Glycerin | 5.0 g |
| Flavouring agent | 0.1 g |
| Ethanol 96% | 10.0 g |
| Distilled water (sufficient to obtain a final volume of 100 ml) | |

Sugar, saccharin and the acid addition salt were dissolved in 60 g of warm water. After cooling, glycerin and a solution of flavouring agents dissolved in ethanol were added. To the mixture water was added to obtain a final volume of 100 ml.

TABLE 2

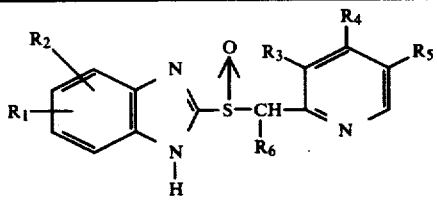

| Ex. | $R_1$ | $R_2$ | $R_6$ | $R_3$ | $R_4$ | $R_5$ | Dose μol/kg | Effect % inhibition |
|---|---|---|---|---|---|---|---|---|
| 1 | 5-$COCH_3$ | 6-$CH_3$ | H | H | $CH_3$ | $CH_3$ | 2 | 90 |
| 4 | 5-$COCH_3$ | 6-$CH_3$ | H | $CH_3$ | $CH_3$ | H | 1 | 60 |
| 7 | 5-$COCH_3$ | 6-$CH_3$ | H | $CH_3$ | H | $CH_3$ | 2 | 100 |
| 8 | 5-$COCH_3$ | 6-$CH_3$ | H | $CH_3$ | $CH_3$ | $CH_3$ | 4 | 100 |
| 9 | 5-$COCH_3$ | 6-$CH_3$ | H | H | $OCH_3$ | H | 2 | 95 |
| 11 | 5-$COCH_3$ | 6-$CH_3$ | H | $CH_3$ | $OCH_3$ | $CH_3$ | 0.5 | 70 |
| x | 5-$COCH_3$ | 6-$CH_3$ | H | H | $CH_3$ | H | 20 | 30 |
| x | 5-$COCH_3$ | 6-$CH_3$ | H | H | H | $CH_3$ | 8 | 80 |
| 2 | 5-$COCH_3$ | 6-$CH_3$ | H | H | $CH_3$ | $CH_3$ | 2 | 60 |
| 5 | 5-$COOCH_3$ | 6-$CH_3$ | H | $CH_3$ | $CH_3$ | H | 2 | 90 |
| 12 | 5-$COOCH_3$ | 6-$CH_3$ | H | $CH_3$ | H | $CH_3$ | 2 | 70 |
| 13 | 5-$COOCH_3$ | 6-$CH_3$ | H | $CH_3$ | $CH_3$ | $CH_3$ | 4 | 80 |
| 14 | 5-$COOCH_3$ | 6-$CH_3$ | H | H | $OCH_3$ | H | 2 | 100 |
| 15 | 5-$COOCH_3$ | 6-$CH_3$ | H | H | $OC_2H_5$ | H | 4 | 75 |
| 16 | 5-$COOCH_3$ | 6-$CH_3$ | H | $CH_3$ | $OCH_3$ | H | 0.5 | 65 |
| 17 | 5-$COOCH_3$ | 6-$CH_3$ | H | $CH_3$ | $OCH_3$ | $CH_3$ | | |
| 18 | 5-$COOCH_3$ | 6-$CH_3$ | H | H | $OCH_3$ | $CH_3$ | 0.5 | 90 |
| x | 5-$COOCH_3$ | 6-$CH_3$ | H | H | H | $CH_3$ | 4 | 50 |
| x | 5-$COOCH_3$ | 6-$CH_3$ | H | Br | H | H | 4 | 0 |
| 6 | 4-$CH_3$ | 6-$CH_3$ | H | $CH_3$ | H | $CH_3$ | 4 | 40 |
| 10 | 4-$CH_3$ | 6-$CH_3$ | H | H | $OCH_3$ | H | 2 | 40 |
| x | 4-$CH_3$ | 6-$CH_3$ | H | H | H | H | 4 | 30 |
| x | 4-$CH_3$ | 6-$CH_3$3 | H | H | H | $CH_3$ | 12 | 50 |
| 3 | 5-$COOCH_3$ | H | H | H | $CH_3$ | $CH_3$ | 4 | 100 |
| 19 | 5-$COOCH_3$ | H | H | $CH_3$ | H | $CH_3$ | 2 | 60 |
| 20 | 5-$COOCH_3$ | H | H | $CH_3$ | $OCH_3$ | $CH_3$ | 0.5 | 65 |
| x | 5-$COOCH_3$ | H | H | H | H | $CH_3$ | 20 | 90 |
| x | 5-$COOCH_3$ | H | H | H | H | H | 20 | 50 |
| 21 | 5-$COCH_3$ | H | H | $CH_3$ | $OCH_3$ | $CH_3$ | 0.5 | 60 |
| x | 5-$COCH_3$ | H | H | H | H | $C_2H_5$ | 20 | 40 |
| 22 | 5-$OCH_3$ | H | H | H | $OCH_3$ | $CH_3$ | | |
| 23 | 5-$OCH_3$ | H | H | $CH_3$ | $OCH_3$ | $CH_3$ | 0.5 | 65 |
| x | 5-$OCH_3$ | H | H | H | $CH_3$ | H | 20 | 10 |
| 24 | 5-$CH_3$ | H | H | $CH_3$ | $OCH_3$ | $CH_3$ | 0.5 | 50 |
| x | 5-$CH_3$ | H | H | H | H | $CH_3$ | 4 | 50 |
| 25 | H | H | H | $CH_3$ | $OCH_3$ | $CH_3$ | 0.5 | 60 |
| x | H | H | H | H | H | H | 4 | 50 |
| 28 | 5-$COOC_2H_5$ | H | H | $CH_3$ | $OCH_3$ | $CH_3$ | 0.5 | 50 |
| 26 | 5-Cl | H | H | $CH_3$ | $OCH_3$ | $CH_3$ | 0.5 | 25 |
| 27 | 5-$CH_3$ | H | H | H | $OC_2H_4OCH_3$ | H | 0.5 | 30 |
| 29 | 5-$COOCH_3$ | H | $CH_3$ | $CH_3$ | H | $CH_3$ | 0.5 | 40 | x denotes a previously known compound

The above given active substance may be replaced with other pharmaceutically acceptable acid addition salts.

EXAMPLE 36

2-[2-(3,4-dimethyl)pyridylmethylsulfinyl]-(5-acetyl-6-methyl)benzimidazole.HCl (250 g) was mixed with lactose (175.8 g), potato starch (169.7 g) and colloidal silicic acid (32 g). The mixture was moistened with 10% solution of gelatin and was ground through a 12-mesh sieve. After drying, potato starch (260 g), talc (50 g) and magnesium stearate (5 g) were added and the mixture thus obtained was pressed into tablets (10.000), with each tablet containing 25 mg of active substance. Tablets can be prepared that contain any desired amount of the active ingredient.

EXAMPLE 37

Granules were prepared from 2-[2-(3,5-dimethyl)-pyridylmethylsulfinyl]-(5-acetyl-6-methyl)benzimidazole-p-hydroxybenzoate (250 g), lactose (175.9 g) and an alcoholic solution of polyvinylpyrrolidone (25 g). After drying, the granules were mixed with talc (25 g), potato starch (40 g), and magnesium stearate (2.50 g) and were pressed into 10.000 tablets. These tablets are first coated with a 10% alcoholic solution of shellac and thereupon with an aqueous solution containing succharose (45%), gum arabic (5%), gelatin (4%), and dyestuff (0.2%). Talc and powedered sugar were used for powdering after the first five coatings. The coating was then covered with a 66% sugar syrup and polished with a solution of 10% carnauba wax in carbon tetrachloride.

EXAMPLE 38

2-[2-(3,5-dimethyl)pyridylmethylsulfinyl]-(5-acetyl-6-methyl)benzimidazole hydrochloride (1 g), sodium chloride (0.6 g) and ascorbic acid (0.1 g) were dissolved in sufficient amount of distilled water to give 100 ml of solution. This solution, which contains 10 mg of active substance for each ml, was used in filling ampoules, which were sterilized by heating at 120° C. for 10 minutes.

I claim:

1. A method of protecting the gastrointestinal tract in a mammal from the untoward, non-gastric-acid-induced effects of exposure to gastrointestinally injurious agents, which comprises:

administering orally to said mammal a non-antisecretory (less than antisecretory ED$_{50}$) amount of a cytoprotective heterocyclylalkylsulfinylbenzimidazole of formula (I)

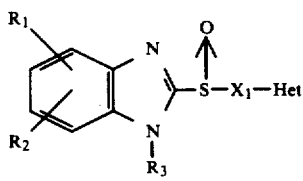

wherein $R_1$, $R_2$, $R_3$, $X_1$ and Het are as defined in claim 8, or a pharmacologically acceptable salt thereof, effective to prevent or ameliorate said effects.

2. A method for the treatment or prevention of a non-gastric-acid induced, non-traumatically-induced, non-neoplastic gastrointestinal inflammatory disease in a mammal suffering from or particularly susceptible to the development of said disease, which comprises:

administering orally to said mammal an amount of a cytoprotective heterocyclylalkylsulfinylbenzimidazole of formula (I)

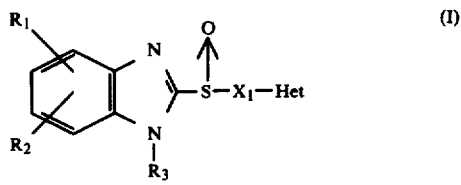

wherein $R_1$ and $R_2$, being the same or different, are
(a) hydrogen,
(b) alkyl of 1 to 4 carbon atoms, inclusive,
(c) fluoro, iodo, chloro, or bromo,
(d) cyano,
(e) carboxy,
(f) carboxyalkyl of 2 to 5 carbon atoms, inclusive,
(g) alkyloxycarbonyl of 2 to 5 carbon atoms, inclusive,
(h) alkoxycarbonylalkyl of 3 to 9 carbon atoms, inclusive, with
the proviso that each alkyl group therein is of 1 to 4 carbon atoms, inclusive,
(i) carbamoyl,
(j) carbamoyloxy,
(k) hydroxy,
(l) alkoxy of 1 to 5 carbon atoms, inclusive,
(m) hydroxyalkyl of 1 to 7 carbon atoms, inclusive,
(n) trifluoromethyl, or
(o) alkylcarbonyl of 1 to 4 carbon atoms, inclusive,
wherein $R_3$ is
(a) hydrogen,
(b) alkyl of 1 to 4 carbon atoms, inclusive,
(c) alkylcarbonyl of 1 to 4 carbon atoms, inclusive,
(d) alkoxycarbonyl of 2 to 5 carbon atoms, inclusive,
(e) carbamoyl,
(f) alkylcarbamoyl of 2 to 5 carbon atoms,
(g) dialkylcarbamoyl of 3 to 9 carbon atoms, inclusive, with the proviso that each alkyl is of 1 to 4 carbon atoms, inclusive,
(h) alkylcarbonylmethyl of 3 to 5 carbon atoms, inclusive,
(i) alkoxycarboylmethyl of 3 to 5 carbon atoms, inclusive, or
(j) alkylsulfonyl of 1 to 4 carbon atoms, inclusive,
wherein $X_1$ is alkylene of 1 to 4 carbon atoms, inclusive, with 1 to 4 carbon atoms, inclusive, in a chain, being straight or branched, and
wherein Het is
(a) imidazolyl,
(b) imidazolinyl,
(c) benzimidazolyl,
(d) thiazolyl,
(e) thiazolinyl,
(f) quinolyl,
(g) piperidyl,
(h) pyridyl, or
(i) imidazolyl, imidazolinyl, benzimidazolyl, thiazolyl, thiazolinyl, quinolyl, piperidyl, pyridyl, or pyridyl substituted by 1, 2, or 3 alkyl of 1 to 4 carbon atoms, inclusive, fluoro, iodo, chloro, or bromo; or wherein R₁ and R₂ are hydrogen, alkyl, halogen, methoxycarbonyl, ethoxycarbonyl, alkoxy, or alkylcarbonyl, being the same or different, R₃ is hydrogen, and -X₁-Het taken together is a moiety of formula (II)

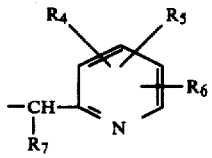

wherein R₄, R₅, and R₆, being the same or different, are (a) hydrogen, (b) methyl, (c) methoxy, (d) ethoxy, (e) methoxyethoxy, or (f) ethoxyethoxy, with the provisos that (1) R₃, R₄, and R₅ are not all hydrogen, and (2) two of R₃, R₄, and R₅ are hydrogen only when the third is not methyl, and wherein R₇ is hydrogen, methyl, or ethyl; or a pharmacologically acceptable salt thereof, effective to treat or prevent said disease and less than the gastric antisecretory ED₅₀ of heterocyclylalkylsulfinylbenzimidazole or salt thereof.

3. A method according to claims 1, or 2 wherein said cytoprotective heterocyclylalkylsulfinylbenzimidazole is selected from the group consisting of:

2-[2-(3,4-dimethyl)-pyridylmethylsulfinyl]-(5-acetyl-6-methyl)benzimidazole,
2-[2-(3,5-dimethyl)-pyridylmethylsulfinyl]-(4,6-dimethyl)benzimidazole,
2-[2-(4,5-dimethyl)-pyridylmethylsulfinyl]-(5-carbomethoxy)benzimidazole,
2-[2-(4,5-dimethyl)-pyridylmethylsulfinyl]-(5-acetyl-6-methyl)benzimidazole,
2-[2-(4,5-dimethyl)-pyridylmethylsulfinyl]-(5-carbomethoxy-6-methyl)-benzimidazole,
2-[2-(3,4-dimethyl)-pyridylmethylsulfinyl]-(5-carbomethoxy-6-methyl)-benzimidazole,
2-[2-(3,5-dimethyl)-pyridylmethylsulfinyl]-(5-acetyl-6-methyl)benzimidazole,
2-[2-(3,4,5-trimethyl)-pyridylmethylsulfinyl]-(5-acetyl-6-methyl)-benzimidazole,
2-[2-(4-methoxy)-pyridylmethylsulfinyl]-(5-acetyl-6-methyl)benzimidazole,
2-[2-(4-methoxy)-pyridylmethylsulfinyl]-(4,6-dimethyl)-benzimidazole,
2-[2-(3,5-dimethyl-4-methoxy)-pyridylmethylsulfinyl]-(5-acetyl-6-methyl)-benzimidazole,
2-[2-(3,5-dimethyl)-pyridylmethylsulfinyl]-(5-carbomethoxy-6-methyl)-benzimidazole,
2-[2-(3,4,5-trimethyl)-pyridylmethylsulfinyl]-(5-carbomethoxy-6-methyl)-benzimidazole,
2-[2-(4-methoxy)-pyridylmethylsulfinyl]-(5-carbomethoxy-6-methyl)-benzimidazole,
2-[2-(4-ethoxy)-pyridylmethylsulfinyl]-(5-carbomethoxy-6-methyl)-benzimidazole,
2-[2-(3-methyl-4-methoxy)-pyridylmethylsulfinyl]-(5-carbomethoxy-6-methyl)-benzimidazole,
2-[2-(3,5-dimethyl-4-methoxy)-pyridylmethylsulfinyl]-(5-carbomethoxy-6-methyl)-benzimidazole,
2-[2-(4-methoxy-5-methyl)-pyridylmethylsulfinyl]-(5-carbomethoxy-6-methyl)-benzimidazole,
2-[2-(3,5-dimethyl)-pyridylmethylsulfinyl]-(5-carbomethoxy)benzimidazole,
2-[2-(3,5-dimethyl-4-methoxy)-pyridylmethylsulfinyl]-(5-carbomethoxy)-benzimidazole,
2-[2-(3,5-dimethyl-4-methoxy)-pyridylmethylsulfinyl]-(5-acetyl)benzimidazole,
2-[2-(4-methoxy-5-methyl)-pyridylmethylsulfinyl]-(5-methoxy)benzimidazole,
2-[2-(3,5-dimethyl-4-methoxy)-pyridylmethylsulfinyl]-(5-methoxy)benzimidazole,
2-[2-(3,5-dimethyl-4-methoxy)-pyridylmethylsulfinyl]-(5-methyl)benzimidazole,
2-[2-(3,5-dimethyl-4-methoxy)-pyridylmethylsulfinyl]-benzimidazole, or
2-[2-(3,5-dimethyl-4-methoxy)-pyridylmethylsulfinyl]-(5-chloro)benzimidazole.

4. A method according to claims 1, or 2 wherein said cytoprotective heterocyclylalkylsulfinylbenzimidazole is selected from the group consisting of:

2-[2-pyridylmethylsulfinyl]benzimidazole,
2-[2-pyridylmethylsulfinyl]-(4,6-dimethyl)benzimidazole,
2-[2-pyridylmethylsulfinyl]-(5-ethyl)benzimidazole,
2-[2-pyridylmethylsulfinyl]-(4-methyl,6-chloro)benzimidazole,
2-[2-pyridylmethylsulfinyl]-(5-methoxy)benzimidazole,
2-[2-pyridylmethylsulfinyl]-(5-hydroxy)benzimidazole,
2-[2-pyridylmethylsulfinyl]-(5-acetyl)benzimidazole,
2-[2-pyridylmethylsulfinyl]-(5-carboxy)benzimidazole,
2-[2-pyridylmethylsulfinyl]-(5-carbethoxy)benzimidazole,
2-[2-(4-chloro)pyridylmethylsulfinyl]benzimidazole,
2-[2-(5-methyl)pyridylmethylsulfinyl]benzimidazole,
2-[2-pyridylmethylsulfinyl]-N-methylbenzimidazole,
2-[2-pyridyl-(methyl)methylsulfinyl]benzimidazole,
2-[2-pyridylmethylsulfinyl]-(4-methyl)benzimidazole,
2-[2-pyridylmethylsulfinyl]-(N-acetyl)benzimidazole,
2-[2-pyridylmethylsulfinyl]-(N-methoxycarbonyl)benzimidazole,
2-[2-pyridylmethylsulfinyl]-(5-methyl)benzimidazole,
2-[2-pyridylmethylsulfinyl]-(5-chloro)benzimidazole,
2-[2-pyridylmethylsulfinyl]-(5-isopropyl)benzimidazole,
2-[2-pyridylmethylsulfinyl]-(5-t-butyl)benzimidazole,
2-[2-pyridylmethylsulfinyl]-(5-n-propyl)benzimidazole,
2-[2-pyridylmethylsulfinyl]-(N-carbamoyl)benzimidazole,
2-[2-pyridylmethylsulfinyl]-(N-methylcarbamoyl)benzimidazole,
2-[2-pyridylmethylsulfinyl]-(N-acetylmethyl)benzimidazole,
2-[2-pyridylmethylsulfinyl]-(N-ethoxycarboylmethyl)benzimidazole,
2-[2-pyridylmethylsulfinyl]-(N-methylsulfonyl)benzimidazole,
2-[2-(4-methyl)pyridylmethylsulfinyl]-(5-methyl)benzimidazole,
2-[2-(5-methyl)pyridylmethylsulfinyl]-(5-methyl)benzimidazole,
2-[2-pyridylmethylsulfinyl]-(6-chloro)benzimidazole,
2-[2-pyridyl-(ethyl)methylsulfinyl]benzimidazole,
2-[2-pyridyl-(ethyl)methylsulfinyl]-(5-chloro)benzimidazole,
2-[2-pyridyl-(methyl)methylsulfinyl]-(5-ethyl)benzimidazole,
2-[2-(3-methyl)pyridylmethylsulfinyl]benzimidazole,
2-[2-(5-ethyl)pyridylmethylsulfinyl]-(5-methyl)benzimidazole, 2-[2-(5-ethyl)pyridylmethylsulfinyl]benzimidazole,
2-[2-pyridyl-(ethyl)methylsulfinyl]-(5-ethyl)benzimidazole,
2-[2-pyridyl-(methyl)methylsulfinyl]-(5-cyano)benzimidazole,
2-[2-pyridyl-(methyl)methylsulfinyl]-(5-trifluoromethyl)benzimidazole,
2-[2-pyridyl-(ethyl)methylsulfinyl]-(5-methyl)benzimidazole,
2-[2-pyridyl-(ethyl)methylsulfinyl]-(5-cyano)benzimidazole,
2-[2-pyridyl-(ethyl)methylsulfinyl]-(5-trifluoromethyl)benzimidazole,
2-[2-pyridylmethylsulfinyl)-(4-chloro)benzimidazole,
2-(2-pyridyl-(isopropyl)methylsulfinyl]benzimidazole,
2-[2-pyridyl-(methyl)methylsulfinyl]-(5,6-dimethyl)-benzimidazole,
and
2-[2-pyridylmethylsulfinyl]-(5,6-dimethyl)benzimidazole.

5. A method according to claim 4 wherein said heterocyclylalkylsulfinylbenzimidazole is 2-[2-pyridylmethylsulfinyl]benzimidazole.

* * * * *